zer et al. ............... 568/487
United States Patent [19]

Griggs et al.

[11] Patent Number: 4,556,744

[45] Date of Patent: Dec. 3, 1985

[54] PROCESS FOR THE PRODUCTION OF ETHANOL AND/OR ACETALDEHYDE BY THE METAL CATALYSED LIQUID PHASE REACTION OF METHANOL, CARBON MONOXIDE AND HYDROGEN IN THE PRESENCE OF A SOLVENT

[75] Inventors: Colin G. Griggs, Ashford; Philip G. Lodge, Woking, both of England

[73] Assignee: The British Petroleum Company p.l.c., London, England

[21] Appl. No.: 658,200

[22] Filed: Oct. 5, 1984

[30] Foreign Application Priority Data

Oct. 8, 1983 [GB] United Kingdom ............... 8326986

[51] Int. Cl.$^4$ ............................................. C07C 45/49
[52] U.S. Cl. ............................... 568/487; 568/902
[58] Field of Search ................................ 568/487, 902

[56] References Cited

U.S. PATENT DOCUMENTS

| | | | |
|---|---|---|---|
| 4,126,752 | 11/1978 | Novotny et al. | 568/902 |
| 4,150,208 | 4/1979 | Pretzer et al. | 568/487 |
| 4,150,246 | 4/1979 | Taylor | 568/902 |
| 4,168,391 | 9/1979 | Slinkard et al. | 568/902 |
| 4,171,461 | 10/1979 | Bartish | 568/902 |
| 4,190,729 | 2/1980 | Forster | 568/487 |
| 4,201,868 | 5/1980 | Slinkard | 568/902 |
| 4,225,517 | 9/1980 | Gane | 568/487 |
| 4,239,705 | 12/1980 | Pretzer et al. | 568/487 |
| 4,239,925 | 12/1980 | Pretzer et al. | 568/487 |
| 4,289,704 | 12/1980 | Pretzer et al. | 568/487 |
| 4,293,718 | 10/1981 | Gauthier-Lafaye et al. | 568/487 |
| 4,304,946 | 12/1981 | Isogai et al. | 568/902 |
| 4,306,091 | 12/1981 | Gauthier-Lafaye et al. | 568/487 |
| 4,337,365 | 7/1982 | Walker | 568/487 |
| 4,361,706 | 11/1982 | Habib | 568/487 |
| 4,361,707 | 11/1982 | Habib | 568/487 |
| 4,374,285 | 2/1983 | Lin et al. | 568/902 |
| 4,374,752 | 2/1983 | Argento et al. | 568/487 |
| 4,389,532 | 6/1983 | Larkins et al. | 568/902 |
| 4,405,815 | 9/1983 | Kiem | 568/487 |
| 4,476,326 | 10/1984 | Lin | 568/487 |

*Primary Examiner*—Werren B. Lone
*Attorney, Agent, or Firm*—Brooks Haidt Haffner & Delahunty

[57] ABSTRACT

A recycle solvent for use in a metal catalysed process for the production of ethanol and/or acetaldehyde by the liquid phase reaction of methanol, carbon monoxide and hydrogen is provided. The solvent should (1) form a single phase with methanol and the liquid products of the process throughout the process; (2) be one in which the catalyst and any associated promoters are soluble; (3) have a boiling point at atmospheric pressure in excess of 120° C. and (4) should be chemically stable under the reaction conditions and not interact in a deliterious manner with either the catalyst or the other components of the reaction. A preferred class of recycle solvent is sulpholane and its substituted derivatives.

9 Claims, No Drawings

PROCESS FOR THE PRODUCTION OF ETHANOL AND/OR ACETALDEHYDE BY THE METAL CATALYSED LIQUID PHASE REACTION OF METHANOL, CARBON MONOXIDE AND HYDROGEN IN THE PRESENCE OF A SOLVENT

The present invention relates to a process for the production of ethanol and/or acetaldehyde by the metal catalysed liquid phase reaction of methanol, carbon monoxide and hydrogen in the presence of a solvent.

The liquid phase reaction of methanol with a mixture of carbon monoxide and hydrogen, generally referred to as synthesis gas, in the presence of metal catalysts, for example a cobalt carbonyl catalyst, is well known, for example see U.S. Pat. No. 2,457,204 issued 28th Dec. 1948 to Richard R. Brooks, and I. Wender et al, Science, Vol. 113, pages 206–207 (1951). In the reported reactions a variety of products are produced including methyl acetate, acetaldehyde, dimethylacetal (also known as 1,1-dimethoxy ethane), ethanol, propanol, isopropanol, isobutanol, ethyl acetate, methane, water and other compounds. The diversity of the resulting products was the major disadvantage of the reaction and since that time considerable research has been directed toward making the reaction more selective in the production of a particular desired product, in particular ethanol and/or acetaldehyde, which are currently produced largely from petroleum derived feedstocks; for example ethanol is obtained from the hydration of ethylene and acetaldehyde from the oxidation of ethylene. Adverse developments in the petroleum industry in recent years have improved the economic prospects and stimulated research into ethanol and acetaldehyde production from methanol and synthesis gas which are derivable from other carbon sources, such as coal and natural gas. As a consequence, during the last decade many patents covering the production of methanol and ethanol via this route have been published. Representative of these patents are U.S. Pat. Nos. 4,126,752; 4,151,208; 4,150,246; 4,171,461; 4,201,868; 4,239,705; 4,239,704; 4,239,925; 4,293,718; 4,304,946; 4,306,091; 4,361,706; 4,361,707; 4,374,285 and 4,389,532 and published U.K. patent applications Nos. 2,083,465, 2,082,181 and 2,088,870.

Although the majority of the publications disclose the use of methanol as the reaction solvent, a few are directed to the addition of a supplementary solvent, principally for the purpose of improving the selectivity of the reaction to one or other of the products. Thus, the complete specification of British Pat. No. 1,546,428 discloses the use of a hydrocarbon solvent, such as alkanes, benzene and alkyl-substituted benzenes. U.S. Pat. No. 4,168,391 discloses the use as solvent of a liquid oxygenated hydrocarbon in which methanol and cobalt carbonyl are soluble under the reaction conditions, which has a dielectric constant less than that of methanol, which does not co-ordinate strongly with cobalt carbonyl, and in which the only oxygen atoms present are ethereal oxygen, oxygen of the hydroxyl group of an alcohol, oxygen of an ester group or oxygen of a ketone group of a ketone, said oxygenated hydrocarbon being a member of the group consisting of 1,4-dioxane, cyclohexanol, 3-pentanone, cyclohexanone, n-butanol, diethylene glycol dibutyl ether, neopentanol, and methyl butyrate.

The solvents described in the above prior art have all been used with the aim of either (i) improving the catalyst productivity by increasing the yields of ethanol or acetaldehyde formed in a given time or (ii) reducing the level of unwanted side products produced by secondary or competing reactions. In a commercial plant however, which will typically operate in either a continuous or semi-continuous manner, the requirements of a solvent are somewhat different and hence the most desirable solvents are somewhat different to those disclosed previously. These differences become particularly important when the role of the solvent is to recycle the catalyst and any associated promoters from the reaction product stream to the reaction vessel in order to preserve catalyst stocks.

A family of solvents has now been discovered which meet all these requirements and hence may be used in commercial metal catalysed processes for the production of ethanol and/or acetaldehyde by the liquid phase reaction of methanol, carbon monoxide and hydrogen.

Accordingly, the present invention provides a recycle solvent suitable for use in a metal catalysed process for the production of ethanol and/or acetaldehyde by the liquid phase reaction of methanol, carbon monoxide and hydrogen characterised in that (1) the solvent forms a single phase with methanol and the liquid products of the process through the process, (2) the solvent is one in which the catalyst and any associated promoters are completely soluble, (3) the solvent has a boiling point at atmospheric pressure in excess of 120° C., (4) the solvent is chemically stable under the reaction conditions and does not interact in a deteterious manner with either the catalyst or the other components of the reaction.

It is an important feature of the recycle solvent that it satisfies all four of the criteria. Thus water, for example while satisfying criteria (1) and (2) does not satisfy either criteria (3) and (4). In particular by interacting with the catalyst it can cause significant catalyst deactivation.

In a similar fashion, solvents such as ethylene glycol, octane, cyclohexane and decane are also not suitable. Such solvents are particularly unsuitable for use as a recycle solvent since, under certain conditions, they form a second phase which is immiscible with the reaction mixture. Thus during the separation of the catalyst/recycle solvent from the reaction products substantial catalyst losses occur through deposition of solids in ancillary apparatus such as distillation columns, pipework etc.

Although suitable recycle solvents should fulfil the four criteria listed above it is preferable that the solvent is also a liquid at room temperature in order to avoid the need for external heating of the catalyst/recycle solvent transfer lines.

The need to fulfil the criteria listed above significantly reduces the number of solvents which may be successfully employed. Examples of suitable solvents include sulpholane, its mono- and di-methyl derivatives and high boiling ethers such as diphenyl ether, ditolyl ether and the like. A preferred solvent is sulpholane.

Methanol is a readily available industrial product. It is generally manufactured on an industrial scale from synthesis gas. Whilst it is preferred that the methanol be substantially pure the presence of small amounts of certain impurities can be tolerated.

Mixtures of the gases hydrogen and carbon monoxide are abundantly available in the form of synthesis gas.

Methods for preparing synthesis gas are well-known in the art and usually involve the partial oxidation of a carbonaceous substance, eg coal. Alternatively synthesis gas may be prepared, for example, by thermal steam reforming of methane. For the purpose of the present invention the molar ratio of carbon monoxide to hydrogen may suitably be in the range 2:1 to 1:3, preferably 3:2 to 2:3 or even more preferably it is 1:1. Methods for adjusting the molar ratio of carbon monoxide to hydrogen are wellknown to those versed in the art. Although it is preferred to use substantially pure synthesis gas the presence of such impurities as carbon dioxide and nitrogen can be tolerated. On the other hand impurities having a deleterious effect on the reaction should be avoided. Thus it may be necessary in a continuously operated process to employ a gas purge to prevent the build-up of deleterious impurities.

The liquid phase reaction of methanol with carbon monoxide and hydrogen is metal catalysed. By metal catalysed is meant that the reaction is catalysed by the metal or a catalytically active compound or complex of the metal either on its own or in combination with other metal co-catalysts or materials which act as promoters. The metal catalyst is suitably a Group VIII metal of which cobalt is preferred. In the case of cobalt, other metal co-catalysts which can be used in conjunction with the catalyst include platinum, ruthenium and rhodium. The atomic ratio of catalyst to co-catalyst is suitably greater than 20:1 preferably in the range 20:1 to 100:1.

Any source of cobalt which will react with carbon monoxide/hydrogen mixtures to yield a cobalt carbonyl or carbonyl hydride complex can be used as catalyst in the process of the present invention. Cobalt is preferably employed in the ionic form, but the use of cobalt metal to react in situ to form ionic cobalt which then further reacts to form the desired cobalt complex is within the scope of the present invention. Typical sources of cobalt are, for example, compounds such as cobalt acetate, cobalt formate, cobalt propionate, cobalt iodide, cobalt carbonyl and the like, which under the reaction conditions form carbonyl hydride complexes. The compounds may be in the hydrated or anhydrous forms. Alternatively there may be used a cobalt complex in which the ligand is derived from cyclopentadiene or a substituted cyclopentadiene as described in our European patent application publication No. 36724.

In general, it is desirable to employ the catalyst in conjunction with a promoter which either increases the overall rate of reaction or minimises the formation of side products. Typically the promoter comprises an iodide promoter and optionally a copromoter.

The iodide promoter is at least one covalent iodide and optionally at least one ionic iodide. Suitable covalent iodides include molecular iodine and either alkyl or aryl iodides, eg methyl iodide. Preferably the covalent iodide is methyl iodide. The ionic iodide may suitably be selected from alkali metal iodides, eg potassium iodide, alkaline earth metal iodides, eg magnesium iodide, ammonium iodide, quaternary ammonium iodides, eg tetramethylammonium iodide, phosphonium iodides, eg triarylphosphine iodide, quaternary phosphonium iodides, eg tetraarylphosphonium iodide, phosphine iodonium iodides and cobalt iodide. Preferably the atomic ratio of iodine to cobalt is about 4:1.

As a co-promoter there may be used a compound of formula $ZRR^1R^2$ wherein R, $R^1$ and $R^2$ are hydrocarbyl groups containing from 1 to 20 carbon atoms which may be in the same or different and Z is one of the elements N, P, As or Sb. The hydrocarbyl group may suitably be a saturated aliphatic, a saturated cycloaliphatic, an aromatic, a substituted saturated aliphatic, a substituted cycloaliphatic or a substituted aromatic group, of which the saturated aliphatic and cycloaliphatic groups and aromatic groups are preferred. The substituents are preferably free from aliphatic carbon-carbon unsaturation and may contain, besides carbon and hydrogen atoms, other atoms such as oxygen, sulphur and halogen, in particular halogen, provided that such atoms are not directly bonded to the Z atom. Illustrative of suitable saturated aliphatic groups are hydrocarbyl groups such as methyl, ethyl, propyl, isopropyl, butyl, isoctyl, decyl, dodecyl, octadecyl, cyclohexyl, cyclopentyl, 3,4-dimethyl cyclopentyl, cyclooctyl, benzyl and $\beta$-phenylethyl. Suitable aromatic groups include hydrocarbyl aromatic groups such as phenyl, tolyl, xylyl, p-ethylphenyl, p-tert-butylphenyl, m-octyl phenyl, 2,4-diethylphenyl, p-phenylphenyl, m-benzylphenyl and 2,4,6-trimethylphenyl. A preferred hydrocarbyl group is the phenyl group. A preferred co-promoter is an amine or a phosphine.

Alternatively there may be used as co-promoter a polydentate ligand wherein the donor atoms are either identical or combinations of dissimilar atoms of the elements nitrogen, phosphorus, arsenic or antimony. Suitable polydentate ligands are described in our European patent application publication No. 10 373.

As regards the molar ratios of the various components, it is desirable that the molar ratio of metal catalyst to methanol is in the range 1:10 to 1:500, preferably from 1:40 to 1:2000. The molar ratio of iodide promoter to metal catalyst is such as to give an atomic ratio of iodine to metal or greater than or equal to 2:1. The molar ratio of metal catalyst to copromoter may be in the range from 2:1 to 1:100, preferably 1:2 to 1:50.

As regards the level of solvent used this will generally be in the range from 5 to 25% by weight based on the weight of methanol used.

The reaction of methanol with synthesis gas may suitably be carried out at a temperature in the range 120° to 250° C., preferably 160° to 210° C., even more preferably at about 170° to 180° C., and at a pressure greater than 50 bars, preferably in the range from 80 to 250 bars.

The process may be carried out semi-continuously or continuously, continuous operation being preferred. The process may be carried out continuously for example by feeding methanol, solvent, catalyst, iodide promoter and co-promoter and synthesis gas to a reactor maintained under reaction conditions, removing from the reactor a liquid product containing acetaldehyde, by-products (e.g. water), unchanged methanol, catalyst, promoters and unreacted synthesis gas, separating the synthesis gas which may be recycled to the reactor, removing light ends, separating by distillation the product containing acetaldehyde, by-products, methanol and other volatile components from the catalyst and solvent and thereafter recovering acetaldehyde from the by-products, there being recycled to the reactor the catalyst, promoter, co-promoter, methanol and solvent. Other reaction by-products, particularly those which can act as precursors for the formation of acetaldehyde, may also be recycled to the reactor with advantage. In order to reduce heavy ends to an acceptable level, it may be necessary from time to time to bleed off a portion of the recycle solvent and add a corresponding amount of fresh solvent. Additionally, it may be necessary to feed from time to time further catalyst.

The residence time may suitably be up to 8 hours, but is preferably in the range from 10 to 180 minutes. Short residence times are preferred because long residence times may lead to further reaction of the acetaldehyde product by aldol condensation-type reaction giving, for example, n-butyraldehyde and/or acetaldol. Within the context of the specification the residence time for batchwise operation is that time during which the reactor is at the specified reaction temperature. When the process is operated continously the residence time is calculated as follows:

Residence Time (hours) =

$$\frac{\text{Volume of the reactor occupied by the liquid phase at STP (liters)}}{\text{Total flow of liquid into the reactor (liters/hour at STP)}}$$

The invention will now be more particularly described by reference to the following Examples.

In the Examples reference will be made to the total realisable yield of acetaldehyde. By this is meant the yield of free acetaldehyde plus the yield of acetaldehyde realisable by the hydrolysis of acetaldehyde-yielding compounds (eg dimethylacetal). In the same way, by realisable methanol is meant the free methanol plus the methanol realisable by the hydrolysis of methanol-yielding esters (eg methyl acetate) plus the methanol realisable by the hydrolysis of dimethyl acetal. Thus, % Molar Yield of Realisable Acetaldehyde =

$$\frac{\text{Moles realisable methanol converted into realisable acetaldehyde} \times 100}{\text{Total moles of realisable methanol fed}}$$

% Molar Yield of acetaldehyde and acetaldehyde-based products (butyraldehyde + acetaldol + dimethylacetal) =

$$\frac{\text{Moles realisable methanol converted into acetaldehyde and acetaldehyde-based products} \times 100}{\text{Total moles of realisable methanol fed}}$$

% Molar Selectivity of Realisable Acetaldehyde =

$$\frac{\text{Moles of realisable methanol converted into realisable acetaldehyde} \times 100}{\text{Total moles of realisable methanol converted}}$$

% Molar Selectivity of acetaldehyde and acetaldehyde-based products =

$$\frac{\text{Moles of realisable methanol converted into acetaldehyde and acetaldehyde-based products}}{\text{Total moles of realisable methanol converted}}$$

and,

Productivity to realisable acetaldehyde (moles/kg final reaction solution/hour) =

$$\frac{(\text{Moles acetaldehyde} + \text{moles dimethylacetal})}{\text{residence time (hours)}} \times \frac{1000}{\text{mass of final reaction solution (grams)}}$$

EXAMPLE 1

A magnetically stirred 300 ml capacity reactor fabricated in Hastelloy B2 (Hastelloy is a registered trade mark) equipped for high pressure reactions was charged with a solution of cobalt (II) iodide dihydrate (0.82 g; 0.0024 mole), tetramethylammonium iodide (0.7 g; 0.0035 mole), triruthenium dodecacarbonyl (0.116 g; 0.018 mmol) and methyl iodide (0.5 g; 0.0035 mole) in methanol (128 g; 4 moles) and sulpholane (40 g; 24% w/w). After purging twice with a 1:1 mixture of carbon monoxide and hydrogen, the autoclave was pressured with this gas to approximately 150 bar. The reactor temperature was rapidly raised to 170° C. and the pressure adjusted to 210 bar. This pressure was then maintained within 5 bar for one hour, after which the autoclave was cooled to room temperature and the reaction products were analysed by gas-liquid chromatography (GLC).

EXAMPLE 2

The reaction solution from Example 1 was distilled to remove all volatile organic compounds and water, thereby leaving a solution of catalyst and promoter in sulpholane. This was added to a fresh charge of methanol (128 g) and methyl iodide (0.5 g). Thereafter the procedure of Example 1 was followed.

EXAMPLE 3

The procedure of Example 2 was repeated using the reaction solution from Example 2 in place of the reaction solution from Example 1.

EXAMPLE 4

The procedure of Example 1 was repeated except that the amount of sulpholane charged to the reactor was reduced from 40 g to 20 g (12% w/w).

EXAMPLE 5

The procedure of Example 2 was repeated using the reaction solution from Example 4 in place of the reaction solution from Example 1.

EXAMPLE 6

The procedure of Example 2 was repeated except that the reaction solution from Example 5 was used in place of the reaction solution from Example 1.

EXAMPLE 7

The procedure of Example 1 was repeated except that the amount of sulpholane added was reduced from 40 g to 10 g (6% w/w). Comparison Test The procedure of Example 1 was repeated except that the addition of sulpholane was omitted.

The yield, the molar selectivity and the productivity to realisable acetaldehyde and the methanol conversion for Examples 1 to 7 and the Comparison Test are given in Table 1.

The yields of major liquid by-products (dimethylether, methyl acetate, ethanol, n-butyraldehyde, ethyl acetate and acetic acid) obtained in Examples 1 and 4 and the Comparison Test are shown in Table 2.

TABLE 1

| Ex. | Comments | Methanol Conversion (%) | Acetaldehyde (Realisable) | | Productivity (moles/kg Solution/hour) |
| | | | Yield (moles) | Molar Selectivity (%) | |
| --- | --- | --- | --- | --- | --- |
| 1 | Sulpholane (40 g, 24% w/w) added | 26.6 | 0.70 | 66.4 | 3.74 |
| 2 | Catalyst recycled from Example 1 | 21.9 | 0.66 | 75.8 | 3.50 |
| 3 | Catalyst recycled from Example 2 | 24.9 | 0.62 | 62.0 | 3.27 |
| 4 | Sulpholane (20 g; 12% w/w) added | 27.5 | 0.73 | 66.7 | 4.30 |
| 5 | Catalyst recycled from Example 4 | 27.6 | 0.63 | 57.1 | 3.72 |
| 6 | Catalyst recycled from Example 5 | 26.0 | 0.65 | 62.3 | 3.82 |
| 7 | Sulpholane (10 g; 6% w/w) added | 28.3 | 0.74 | 65.4 | 4.58 |
| Comp Test | Sulpholane addition omitted | 30.0 | 0.74 | 61.9 | 4.87 |

TABLE 2

| Example | Comments | By-products yields (moles) | | | | | |
| | | dimethyl-ether | methyl acetate | ethanol | n-butyraldehyde | ethyl acetate | acetic acid |
| --- | --- | --- | --- | --- | --- | --- | --- |
| 1 | Sulpholane (40 g; 24% w/w) added | 0.026 | 0.16 | 0.034 | 0.006 | 0.0019 | 0.0081 |
| 4 | Sulpholane (20 g; 12% w/w) added | 0.06 | 0.13 | 0.025 | 0.004 | 0.0008 | 0.014 |
| Comp Test A | Sulpholane addition omitted | 0.10 | 0.11 | 0.023 | 0.004 | 0.0006 | TRACE |

Inspection of Tables 1 and 2 shows that the catalyst and promoters can be recycled in sulpholane as the solvent without substantial losses in activity and without substantial changes in by-product distributions, ie that sulpholane behaves as an inert solvent.

COMPARATIVE TEST B

This test illustrates the use of γ-butyrolactone as a solvent for the reaction. γ-butyrolactone is not a solvent according to the present invention as it undergoes decomposition under the reaction conditions.

A Hastelloy B2 autoclave (Hastelloy is a registered trade mark) was charged with the following:

| | |
| --- | --- |
| Cobalt iodide | 0.82 g |
| Triruthenium dodecacarbonyl | 0.012 g |
| Methyl iodide | 0.5 g |
| Tetramethylammonium iodide | 0.7 g |
| Methanol | 128 g |
| γ-Butyrolactone | 40 g |

After purging twice with a 1:1 mixture of carbon monoxide and hydrogen, the autoclave was pressured with the same gas maxture to 150 bar. The reactor temperature was rapidly raised to 170° C. and the pressure adjusted to 210 bar. This pressure was then maintained within 5 bar for one hour, after which the autoclave was cooled to room temperature and the reaction products analysed by gas-liquid chromatography (GLC). After analysis, the reaction mixture was distilled to leave as residue the catalyst, its associated solvent and trace amounts of high boiling products.

COMPARATIVE TEST C

The residue recovered from Comparative Test B was recycled to the autoclave along with 0.5 g of fresh methyl iodide and 128 g of fresh methanol. The weight of residue recycled was 40.45 g (41.64 g theoretical based on quantities added in Comparative Test B). After addition, the experimental procedure of Comparative Test B was repeated.

COMPARATIVE TEST D

The residue recovered from Comparative Test C was recycled to the autoclave along with 0.5 g of fresh methyl iodide and 128 g of fresh methanol. The weight of residue recycled this time was 33.52 g (41.64 g theoretical). After addition the experimental procedure of Comparative Test B was repeated.

COMPARATIVE TEST E

Comparative Test B was repeated except that 40 g of ethylene glycol was used in place of γ-Butyrolactone. At the end of the reaction an attempt was made to remove the reaction products and water by distillation. During the final stages of distillation, two liquid phases were formed and substantial amounts of the catalyst were deposited on the walls of the distillation unit. No catayst recycle was attempted due to such losses.

TABLE 3

| Comparative Test | Comments | Methanol conversion (%) | Acetaldehyde (Realisable) | | Productivity ethyl (moles/Kg solution 1 hr) |
| | | | Yield (moles) | Molar Selectivity (%) | |
| --- | --- | --- | --- | --- | --- |
| B | γ-Butyrolactone solvent | 27.3 | 0.648 | 59.33 | 3.46 |
| C | B recycle | 31.7 | 0.601 | 45.90 | 3.30 |
| D | C recycle | 33.1 | 0.578 | 43.64 | 3.24 |
| E | Ethylene glycol solvent | 41.5 | | 21.1 | 1.87 |

We claim:

1. A process for the preparation of acetaldehyde, ethanol or mixtures thereof which process comprises reacting methanol, carbon monoxide and hydrogen at an elevated temperature and pressure in the presence of a cobalt catalyst wherein (1) in a carbonylation stage the methanol is reacted with the carbon monoxide and hydrogen in the presence of the cobalt catalyst and, as a recycle solvent, sulpholane or a substituted derivative thereof, (2) in a separation stage the reaction products and unreacted methanol are separated from the cobalt catalyst and the recycle solvent, and (3) in a recycle stage the catalyst and recycle solvent are recycled to the carbonylation stage.

2. A process as claimed in claim 1 characterised in that the catalyst also includes an iodide promoter.

3. A process as claimed in claim 2 characterised in that the catalyst also includes a copromoter.

4. A process as claimed in claim 2 wherein a metal co-catalyst selected from the group consisting of ruthenium and platinum is also used.

5. A process as claimed in claim 1 characterised in that it is carried out either continuously or semi-continuously.

6. A process as claimed in claim 1 wherein the reaction is carried out at a temperature in the range 160° to 210° C.

7. A process as claimed in claim 1 wherein the reaction is carried out at a temperature in the range 170° to 180° C.

8. A process as claimed in claim 1 wherein the sulpholane derivative is a monomethyl-sulpholane or a di-methyl-sulpholane.

9. A process as claimed in claim 1 wherein the level of recycle solvent is from 5 to 25% by weight based on the weight of methanol used.

* * * * *